United States Patent

[19]

Ravas

[11] 4,056,105
[45] Nov. 1, 1977

[54] PULSE GENERATOR

[75] Inventor: Richard J. Ravas, Monroeville, Pa.

[73] Assignee: Westinghouse Electric Corporation, Pittsburgh, Pa.

[21] Appl. No.: 525,123

[22] Filed: Nov. 19, 1974

[51] Int. Cl.$^2$ .............................................. A61N 1/36
[52] U.S. Cl. ..................... 128/419 PG; 128/419 PS; 128/423 R
[58] Field of Search .................. 128/419 BG, 419 PS, 128/419 R, 421, 422, 423

[56] References Cited

U.S. PATENT DOCUMENTS

| | | | |
|---|---|---|---|
| 3,241,557 | 3/1966 | Masaki | 128/422 |
| 3,442,269 | 5/1969 | Druz | 128/419 D |
| 3,707,974 | 1/1973 | Raddi | 128/419 PG |
| 3,898,994 | 8/1975 | Kolenik | 128/419 PG |

Primary Examiner—William E. Kamm
Attorney, Agent, or Firm—D. C. Abeles; Z. L. Dermer

[57] ABSTRACT

A DC pulse generator, specifically suitable for application as a cardiac pacemaker having a substantially constant energy output which is independent of the output load. The output pulse is derived from a capacitive reactance which is partially discharged to a preselected reference level. The cyclic rate of discharge is maintained substantially constant, and accordingly, the pulse width is varied to assure a constant energy output to the load. The capacitive reactance is charged in between output pulse periods from a matched impedance radioisotope thermoelectric source through a constant current inverter, step-up transformer, voltage doubler, inverter network. The oscillator controlling cyclic discharge of the capacitance through the load and the inverter, which is arranged in a push-pull configuration, is designed to be self-starting to avoid stall conditions during operation. Furthermore, the discharge rate is substantially independent of the DC level and provides a negative rectangular output pulse. In the event external defibrillator pulses are applied, means are provided to conduct resulting current impulses directly into the capacitive reactance which can safely absorb the energy, thus avoiding failures in the internal circuitry elements.

5 Claims, 1 Drawing Figure

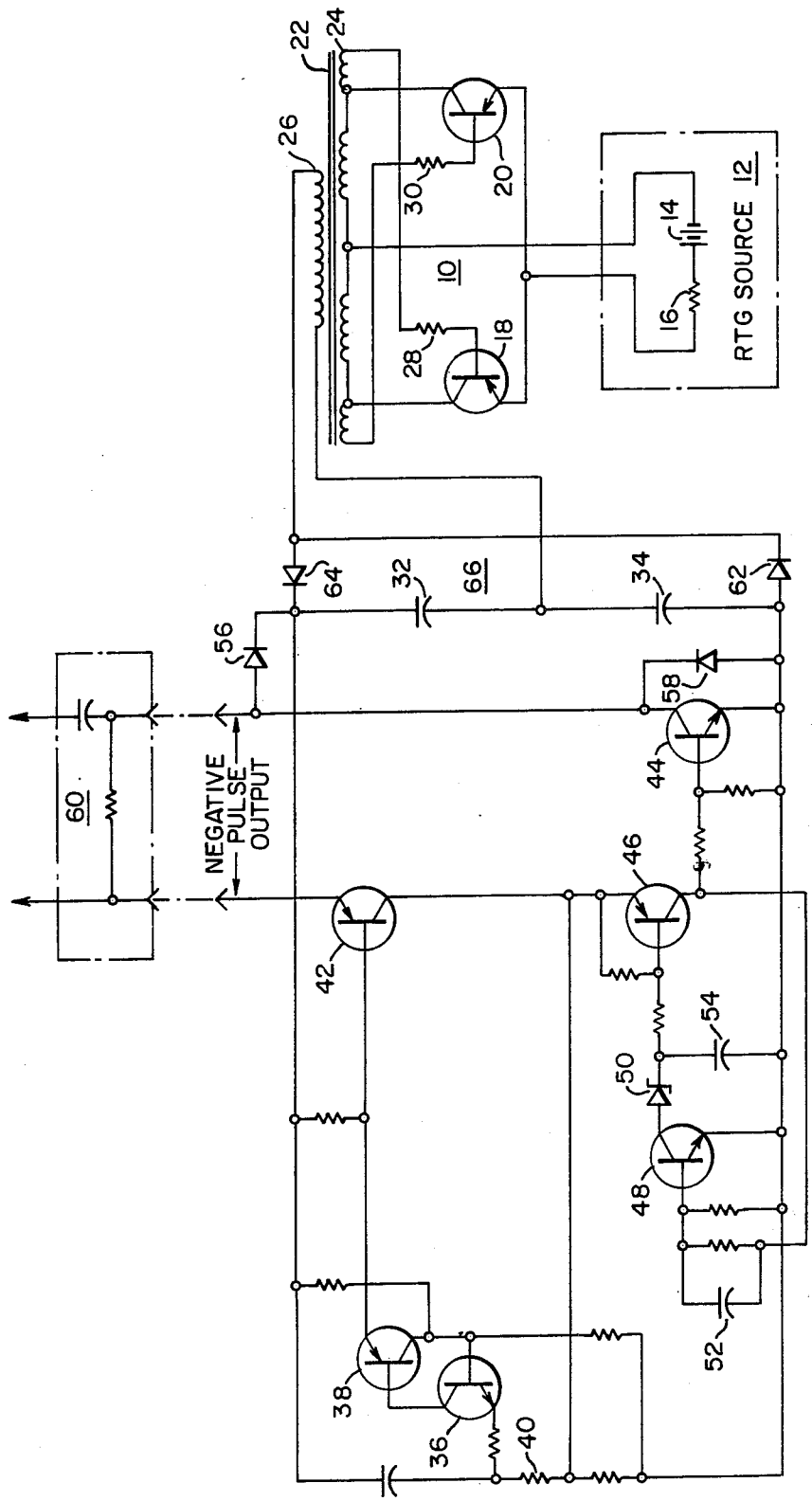

PULSE GENERATOR

BACKGROUND OF THE INVENTION

This invention pertains generally to DC pulse generators having a substantially constant energy pulse output and more specifically to such generators that can be employed in combination with radioisotopic thermoelectric generators in cardiac pacemaker applications.

The use of implanted battery powered pacemakers has become a common medical procedure for alleviating the effects of Stokes-Adams disease. Persons having this disease exhibit an abnormally slow pulse rate due to the breakdown of the body's natural heart stimulating mechanism. By electrically stimulating the heart with very low energy electrical impulses, it can be made to resume a normal pulse rate and thus the patient can lead a more normal life. The use of battery power has presented a major drawback in pacemaker design due to its finite storage capacity. Surgical replacement is required at intervals ranging between six months and three years for most pacemakers. Moreover, the output pulse energy must be kept as small as possible to minimize battery drain and this sometimes allows little margin between the available pulse energy and the minimum exciting threshold of the heart. Obviously, a better power source is needed.

Radioisotope thermoelectric generators similar to those employed in spacecrafts for long duration power sources are a desirable alternative for this application. A decaying radioisotope material produces heat which is converted by a thermoelectric element into a low voltage power source. Such a system will operate for ten years with only about a ten percent drop in power output, thus exhibiting a dramatic advantage over the battery sources conventionally employed.

There are, unfortunately, some limitations to employing radioisotope thermoelectric generator systems. Probably, the most significant limitation is an economic one. There is a limited source of the necessary isotope available and thus its cost is the major factor in the cost of the pacemaker. The ultimate number of such units which can be manufactured is also limited in view of the rarity of the isotope. Accordingly, it is desirable to optimize the pacemaker energy conversion to achieve an acceptable design. Presently there are several radioisotope thermoelectric generator pacemakers being manufactured, however their efficiencies are extremely low ranging between sixteen and nineteen percent. Accordingly, a more efficient pacemaker is required if radioisotopic sources are to be continually employed in pacemaker applications.

The output pulser in most pacemakers is nearly identical in operation and accounts for a major part of the system's loses. Conventionally, pacemakers charge a 3.3 microfarad capacitor to six volts, which is subsequently discharged into the heart. The capacitor is completely emptied each pulse thus precisely metering sixty microjoules of energy into the heart independent of the impedance of the output load. Each time the capacitor is recharged, the charging resistance dissipates as much energy as the capacitor receives, resulting in a fifty percent system charging loss. An apparent alternative is to apply a fixed voltage square wave pulse to the load every cycle and thus avoid complete capacitor recharging. This is undesirable from a medical viewpoint since the output energy per pulse would then vary inversely to the impedance of the output load, and the heart's impedance, while normally three hundred ohms, can easily vary from one hundred to one thousand ohms. Accordingly, a new approach to the output pulser is required if an overall improvement in efficiency is to be obtained.

SUMMARY OF THE INVENTION

Briefly, this invention provides an improved DC pulse generator having a substantially constant energy pulse output which is independent of the output load and specifically suitable for cardiac stimulation. The pulse output is derived from a capacitive reactance which is cyclically discharged to the load. A source of electrical energy is connected to charge the capacitance to the desired output pulse voltage level. The capacitive reactance is disconnected from the load during the period of each cycle of charge. During the output pulse interval the capacitive reactance is connected to the load which discharges the reactance to a preselected reference voltage level. Desirably, the capacitor is charged from a matched impedance source so that the output pulse width is adjusted to keep the system in energy equilibrium while the pulse rate is maintained substantially constant. Preferably, the charging source is derived from a radioisotope thermoelectric generator and the charging and cyclic discharge circuits are designed to be self-starting to assure the longevity and reliability of the pulser's operation.

BRIEF DESCRIPTION OF THE DRAWINGS

For a better understanding of the invention, reference may be had to the preferred embodiment, exemplary of the invention, shown in the accompanying drawing which illustrates a schematic circuitry arrangement exemplary of one mode of practicing this invention.

DESCRIPTION OF THE PREFERRED EMBODIMENT

As a preferred arrangement for minimizing intervals of surgical replacement, this invention will be described in combination with a radioisotope thermoelectric generator source to satisfy cardiac pacemaker requirements. Such radioisotope thermoelectric generators are well known in the art having previously been developed for spacecraft applications. Optimized designs are generally known which will produce an output of 0.25 to 0.50 volts into a matched impedance load. In other words, the thermoelectric source is electrically equivalent to a 0.5 to 1.0 volt source in series with a resistor approximately equal to that of the designed load. Inasmuch as the output voltage pulse must be of the order of six volts in amplitude in order to meet the minimum exciting threshold of the heart a DC-DC converter, preferably including an inverter, step-up transformer, and rectifier is required to provide the needed voltage amplification.

In accordance with this embodiment, the radioisotope thermoelectric generator power conditioning system includes a push-pull inverter, which is superior to a single ended configuration in that it draws a nearly contant current during each complete cycle of oscillation and thus maintains continuously matched loading of the radioisotope thermoelectric generator. The inverter transistors, operating at low voltage, commonly account for a major share of the system losses. To increase the overall efficiency of the device the transistors are overdriven and operated well below their normal current ratings reducing the collector-emitter saturation voltage level to approximately 50 millivolts. Desirably, the use of silicon inverter transistors is avoided since their base-emitter junction voltage of approximately 0.6 volts will cause excessive drive loss and further, since this voltage is more than a factor of two larger than the normal inverter input voltage from the radioisotope thermoelectric generator source, self-startup would be impossible. For these reasons, it is desirable to employ germanium transistors which do not present any thermal problem inasmuch as they operate at a low power level and are kept at body temperature in a pacemaker application.

An unusual transformer design problem exists due to the extremely low power required in this particular application. Although a very small diameter core of Supermalloy material is employed for the transformer to accommodate the pacemaker size, the magnetomotive force required to drive the flux around the core is still quite large. It does in fact account for another of the major system losses. It is possible to reduce its effect by increasing core size to allow more turns, inasmuch as the required magnetomotive force increases linearly with diameter while the turns increase as the square. In view of the fact that size and weight are important considerations in this particular application the transformer is a design compromise considering all these factors.

In this particular embodiment the output of the transformer is a voltage doubler network 66 employing two germanium diodes 62 and 64 illustrated in the FIGURE. A full six volt output winding was experimentally found to increase the transformer size unnecessarily while a smaller winding with more rectifier multiplication would only cause slightly higher diode losses. Germanium diodes are desirably employed rather than silicon units due to their lower forward voltage drops permitting higher system efficiencies.

The output pulse to be communicated to the heart is obtained in accordance with this invention by monitoring the voltage of a DC-DC link capacitor and constantly adjusting the output square wave pulse width so that the link capacitor voltage remains at or above a predetermined level. Since the radioisotope thermoelectric generator is a matched impedance source, the link capacitor voltage will ratchet up if the output pulse energy is too low or it will ratchet down if the output pulse energy is too high. Hence, the system output pulse width is adjusted to keep the system in energy equilibrium. Inasmuch as complete dissipation of the charge of the capacitor does not occur during the period of any output pulse cycle, system losses are minimized.

A schematic of an exemplary circuit designed in accordance with this invention is illustrated in the single FIGURE of the attached drawing. The low voltage inverter 10 used to boost the 0.25 volt radioisotopic generator source 12 to a 7 volt output is basically a Royer circuit using Supermalloy as the magnetic material in the saturable transformer 22. Since the thermoelectric source 12 is electrically equivalent to a battery 14 in series with a resistor 16 approximately equal to the impedance of the designed load it is desirable to design the inverter to present a constant current load to the radioisotope thermoelectric generator. If a circuit arrangement other than the push-pull inverter illustrated was employed, such as a single ended flyback circuit, an additional capacitor input filter would be required to satisfy the constant input current requirements.

The inverter transistors 18 and 20 are operated in an overdriven mode so that the collector-emitter saturation voltage levels approach zero volts and thus, they become nearly ideal switches. In this particular embodiment, germanium devices are used rather than silicon because their base-emitter voltage drop must be less than the 0.5 volt open circuit value for the radioisotope thermoelectric generator source to self-start, and their base drive power is lower.

The inverter transformer 22 illustrated is preferably of a Supermalloy type, because at the available power level, the magnetomotive force of the other core materials would cause intolerable core losses. The core used is a compromise between efficiency and size. Although a larger core could yield a more efficient transformer, for a particular application to cardiac pacemakers it is necessary to satisfy reasonable size limitations as previously explained.

The biasing necessary to drive transistors 18 and 20 is achieved by cross-coupling the resistors 28 and 30 through a portion of the secondary winding 24 of the transformer. The windings assure that the transistors are periodically driven completely into saturation. The inverter illustrated is self-starting, due to the interaction of the inverter circuit elements with the radioisotope thermoelectric generator source resistance. In the event of any stall condition, the transistors 18 and 20 are automatically biased into a class A region needed to initiate oscillation. Thus, the final output voltage across the transformer secondary winding 26 is a reasonably good square wave in spite of the soft saturating character of the magnetic material.

The output of the Royer inverter circuit 10 is used to charge two DC link capacitors 32 and 34, which are arranged in series to provide a seven volt DC link level. The charging current is rectified through a voltage doubler circuit 66 by the diodes 62 and 64.

Transistors 36 and 38, and associated components form a relaxation oscillator based on the equivalent circuit of a programmable unijunction transistor. The frequency of oscillation of this oscillator is the pulse rate of the pacer and may be adjusted by altering the value of resistor 40. The frequency of oscillation is nearly independent of the DC supply level, having a very slight tendency for the frequency to increase for an extreme drop in the input voltage supply. The relaxation oscillator is self-starting and the avoidance of stall conditions is assured by the feedback loop incorporating transistor 42, which prevents a latch-on condition. Transistor 42 also provides an amplification of current level as is needed to drive the output transistor 44.

Transistor 46 acts as a level comparator which conducts drive current to the output transistor 44 as long as the DC link capacitor voltage exceeds a predetermined reference level. Whenever the DC link voltage drops below this level, the output transistor 44 base drive is interrupted. The DC link capacitor is then recharged during the "off" interval in anticipation of the next pulse. In this way the output pulse length is always adjusted to match the radioisotope thermoelectric generator source capability.

One problem commonly encountered in such a low power and low voltage circuit is that the voltage reference element illustrated by Zener diode 50 causes excessive circuit dissipation. Ideally, it is preferable to have a reference voltage of approximately 5.6 volts, but moderate variations can be tolerated. Ordinarily low voltage Zener diodes do not provide a sharp "knee" in the range of one microampere as is desired in this system. Recently, Zener diodes having the desired characteristics have become available and this now presents very little problem. Alternately, a transistor, such as one of the 40235 type, can be employed in an equivalent Zener diode circuit to exhibit a well defined 5.8 volt Zener knee below one microampere. The transistor is an RF type with corresponding narrow base width etc., and thus possesses the desired avalanche characteristics. As a further precaution against diode leakage problems, transistor 48 is provided to connect the reference diode to the circuit only during the duration of the output pulse and thus one can tolerate somewhat higher diode leakage without excessive circuit dissipation. The two capacitors 52 and 54 are used only to provide the initial starting impulse to the network in anticipation of the Zener diode's reaction.

Two diodes 56 and 58 have been added to the pacemaker as a means to overcome failures to the circuit in the event external defibrillator pulses are applied. The diodes route the defibrillator current impulses into the DC link capacitors which can safely absorb the energy.

There is some disagreement between authorities in the field as to the output pulse characteristic desired for a pacemaker. The major controversy centers on whether the pulse should be unidirectional or bidirectional. Apparently the biggest concern is whether a DC flow through the electrodes is tolerable. In some cases, severe electrolysis of the electrodes has been reported, but others have reported that proper electrode materials will correct this problem. Since the pulser of this invention is of the DC type, it can be modified by the resistor capacitor network 60 to an AC type, if the electrolysis problem exists. Since the values of the resistor and capacitor, which form part of the network 60, are both large relative to the load impedance and the conventional output capacitance, generally 3.3 microfarads, these components will negligibly alter the system output energy or waveform.

Accordingly, an extremely efficient pulse generator is provided adaptable for application as a cardiac pacemaker having a fifty percent reduction in power requirement as compared to conventional units presently on the market.

I claim as my invention:

1. A radioisotope thermoelectric heart pacemaker comprising:
    a radioisotope thermoelectric DC source;
    a substantially constant input current inverter electrically connected to be driven by the source and having a square wave output;
    a transformer having a primary winding connected to the square wave output and a secondary winding output;
    a voltage multiplier rectifier having an input from the transformer secondary winding and an output;
    a capacitive reactance, having an output which is adapted to be connected to the heart, comprising a plurality of series coupled capacitors respectively connected in parallel across the secondary winding through the rectifier in a manner that will provide a voltage across the reactance equal to the secondary winding output multiplied by the number of capacitors;
    means for monitoring the voltage level across the capacitive reactance and comparing the monitored voltage with a preselected fixed reference level; and
    means connected between the capacitive reactance and the output to the heart for cyclically discharging the capacitive reactance through the heart at a substantially constant rate, said discharge means being responsive to said monitoring means to disconnect the capacitive reactance from the heart during the discharge portion of each cycle prior to substantial discharge of the reactance when the voltage across the reactance drops below the preselected reference level.

2. The pacemaker of claim 1 wherein the cyclic frequency of the discharge means is substantially constant and substantially independent of the energy level of the source.

3. The pacemaker of claim 2 wherein the cyclic operation of the discharge means is self-starting.

4. The pacemaker of claim 1 including means for disconnecting the monitoring means from the capacitive reactance while the capacitive reactance is not discharging to the heart.

5. A radioisotope thermoelectric heart pacemaker comprising:
    a radioisotope thermoelectric DC source;
    a substantially constant input current inverter electrically connected to be driven by the source and having a square wave output;
    a transformer having a primary winding connected to the square wave output and a secondary winding output;
    a voltage multiplier rectifier having an input from the transformer secondary winding and an output;
    a capacitive reactance, having an output which is adapted to be connected to the heart, comprising a plurality of series coupled capacitors respectively connected in parallel across the secondary winding through the rectifier in a manner that will provide a voltage across the reactance equal to the secondary winding output multiplied by the number of capacitors;
    means for monitoring the voltage level across the capacitive reactance;
    means connected between the capacitive reactance and the output to the heart for cyclically discharging the capacitive reactance through the heart, said discharge means being responsive to said monitoring means to disconnect the capacitive reactance from the heart during the period of each cycle prior to substantial discharge of the reactance when the voltage across the reactance drops below a preselected reference level; and
    means for routing external defibrillator current impulses, applied to the heart output, directly to the capacitive reactance.

* * * * *